(12) United States Patent
Jones et al.

(10) Patent No.: US 6,412,483 B1
(45) Date of Patent: *Jul. 2, 2002

(54) OXYGEN BLENDING IN A PISTON VENTILATOR

(75) Inventors: Michael B. Jones, Excelsior; Eric Bailey, Roseville; David B. Lura, Brooklyn Park, all of MN (US)

(73) Assignee: Nellcor Puritan Bennett, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/573,453

(22) Filed: May 16, 2000

Related U.S. Application Data

(63) Continuation of application No. 09/007,853, filed on Jan. 15, 1998, now Pat. No. 6,076,523.

(51) Int. Cl.[7] .............................. A62B 7/00; A62B 9/00; G05B 1/00

(52) U.S. Cl. ............................. 128/205.11; 128/204.21; 128/204.22; 128/205.18

(58) Field of Search ..................... 128/200.24, 204.18, 128/204.21, 204.22, 204.23, 205.11, 205.18, 205.24

(56) References Cited

U.S. PATENT DOCUMENTS

| | | | |
|---|---|---|---|
| 3,741,208 A | | 6/1973 | Jonsson et al. |
| 4,022,234 A | | 5/1977 | Dobritz |
| 4,023,587 A | | 5/1977 | Dobritz |
| 4,323,064 A | | 4/1982 | Hoenig et al. |
| 4,527,557 A | | 7/1985 | DeVries et al. |
| 4,587,967 A | | 5/1986 | Chu et al. |
| 4,617,637 A | * | 10/1986 | Chu et al. .................... 364/505 |
| 4,651,726 A | | 3/1987 | Gupta et al. |
| 4,794,922 A | | 1/1989 | DeVries |
| 5,005,570 A | * | 4/1991 | Perkins .................... 128/204.23 |
| 5,072,729 A | | 12/1991 | DeVries |
| 5,150,291 A | | 9/1992 | Cummings et al. |
| 5,161,525 A | | 11/1992 | Kimm et al. |
| 5,237,987 A | | 8/1993 | Anderson et al. |
| 5,271,389 A | | 12/1993 | Isaza et al. |
| 5,299,568 A | | 4/1994 | Forare et al. |
| 5,319,540 A | | 6/1994 | Isara et al. |
| 5,331,995 A | | 7/1994 | Westfall et al. |

(List continued on next page.)

FOREIGN PATENT DOCUMENTS

| | | |
|---|---|---|
| EP | 0042321 | 12/1981 |
| EP | 0056148 | 7/1982 |
| WO | WO 9624402 | 8/1996 |

OTHER PUBLICATIONS

Dräger Inc. Critical Care Systems—Minimum Pressure Ventilation brochure.

(List continued on next page.)

Primary Examiner—John G. Weiss
Assistant Examiner—Joseph F. Weiss
(74) Attorney, Agent, or Firm—Hovey Williams LLP

(57) ABSTRACT

A piston ventilator is disclosed herein which uniquely includes an oxygen blending module which supplies oxygen enhancement for aiding patients requiring respiratory treatment. The oxygen blending module supplies a preselected enrichment of oxygen to a piston and cylinder assembly wherein the amount of oxygen permitted to flow therein is continuously monitored and controlled according to the volume above the piston in the cylinder as calculated by a controller. The oxygen blending module includes a flow sensor which monitors the flow of supplemental oxygen into the piston and cylinder assembly, and further includes a primary oxygen control valve which restricts the flow of oxygen through the flow sensor to the piston and cylinder assembly depending on the difference between the calculated desired amount of oxygen and the target amount of oxygen provided to the controller.

12 Claims, 2 Drawing Sheets

U.S. PATENT DOCUMENTS

| | | | | |
|---|---|---|---|---|
| 5,383,449 A | | 1/1995 | Forare et al. | |
| 5,390,666 A | | 2/1995 | Kimm et al. | |
| 5,452,714 A | * | 9/1995 | Anderson et al. | 128/205.11 |
| 5,494,028 A | | 2/1996 | DeVries et al. | |
| 5,507,282 A | | 4/1996 | Younes | |
| 5,524,615 A | | 6/1996 | Power | |
| 5,664,560 A | * | 9/1997 | Merrick et al. | 128/203.25 |
| 5,664,562 A | | 9/1997 | Bourdon | |
| 5,701,883 A | * | 12/1997 | Hete et al. | 128/204.26 |
| 5,722,449 A | * | 3/1998 | Heinonen et al. | 137/101.19 |
| 5,752,506 A | | 5/1998 | Richardson | |
| 6,076,523 A | * | 6/2000 | Jones et al. | 128/205.11 |
| 6,116,240 A | * | 9/2000 | Merrick et al. | 128/203.25 |
| 6,123,074 A | * | 9/2000 | Hete et al. | 128/205.11 |

OTHER PUBLICATIONS

Newport Medical Instruments Inc.—Newport Wave VM200 brochure; Feb. 1995.

Newport Medical Instruments Inc.—The Newport Breeze EI50 Ventilator brochure; Mar. 1996.

Allied Healthcare Products, Inc.—The Bear 1000 Ventilator with Smart Trigger brochure; 1996.

Healthdyne Technologies—Quantum PSV brochure.

Bird Products Corporation—TBird AVS Advanced Ventilatory System brochure; Jan. 1996.

Healthdyne International—Quantum PSV brochure.

Respironics Inc.—BiPAP Vision System brochure; 1996.

Lifecare International, Inc.—PLV–102 brochure; Jan. 1995.

Air Liquide Healthcare—Taema Monnal DCC brochure.

Bird Products Corporation—TBird VS TBird $VSO_2$ Ventilatory System brochure; Jan. 1996.

* cited by examiner

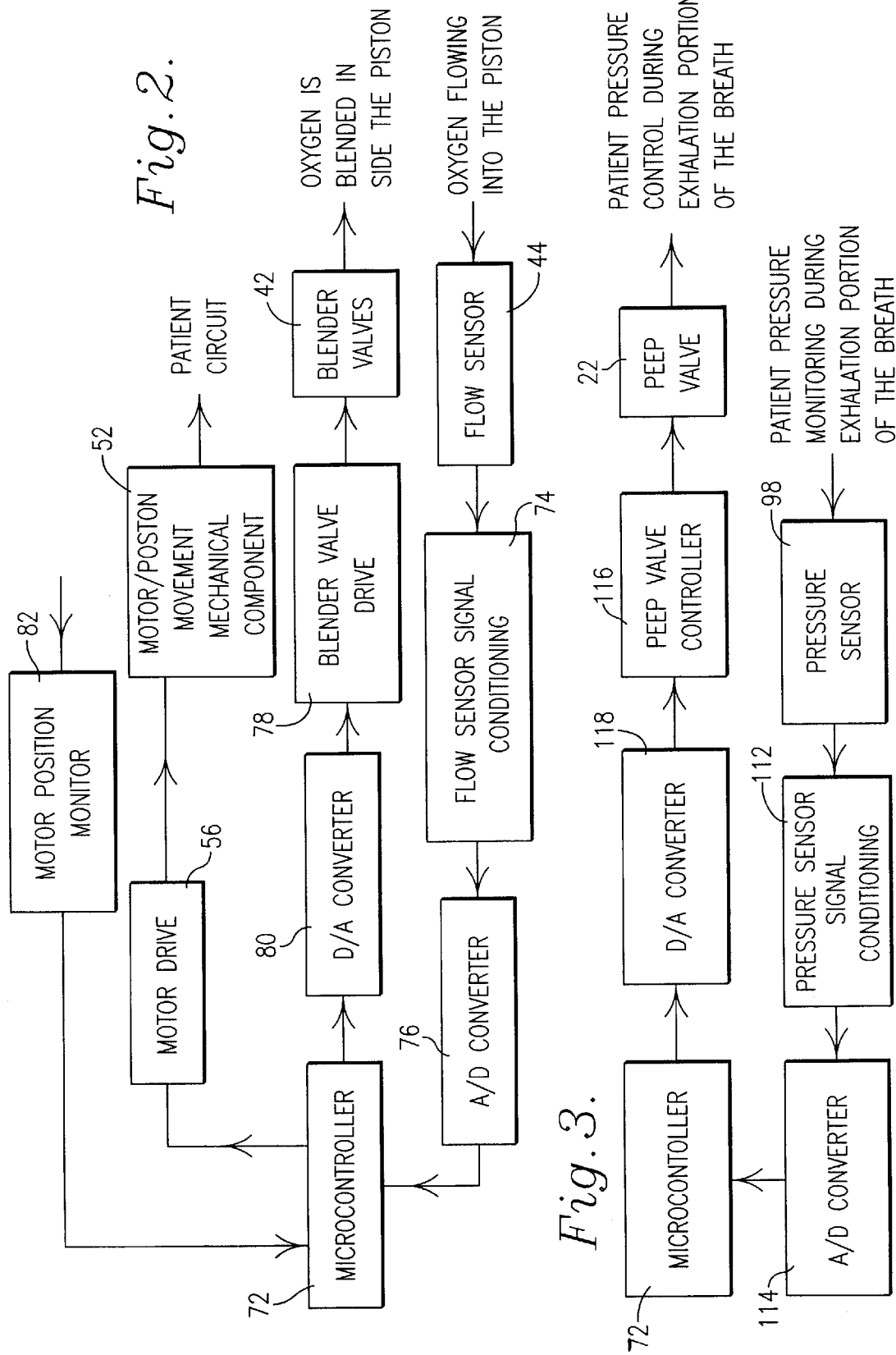

OXYGEN BLENDING IN A PISTON VENTILATOR

RELATED APPLICATION

This application is a continuation of U.S. patent application Ser. No. 09/007,853, filed Jan. 15, 1998, issued Jun. 20, 2000, as U.S. Pat. No. 6,076,523.

BACKGROUND OF THE INVENTION

1. Field of the Invention

This invention relates to a method and apparatus for blending oxygen, in a piston-type ventilator which permits constant and accurate supply of supplemental oxygen to the user through a closed loop pressure support ventilation system. More particularly, it is concerned with a piston ventilator used to ventilate patients having difficulty respirating, which adjusts the amount of oxygen supplied both to the piston cylinder and to the patient circuit for ensuring a satisfactory oxygen content throughout the air in the circuit inhaled by the patient.

2. Description of the Prior Art

Ventilation systems are designed to supply air at a pressure greater than atmospheric pressure to assist in breathing, and may include systems which provide supplemental oxygen which is blended with air to enrich the gas which is inhaled. Such systems are typically employed for patients with respiratory ailments wherein the oxygen-enriched air is provided by blending bottled air or less often atmospheric air with supplemental oxygen in a controlled manner for each breath.

Another system for mixing the oxygen with air or another gas in a ventilation system in predetermined proportions involves the use of separate inlets into a pressure vessel up to respective first and second pressures is described in U.S. Pat. Nos. 4,022,234 and 4,023,587. The system shown therein operates in alternating withdrawal and mixing cycles. A feedback control of the rate of flow and pressure of breathing gas to a patient by an inspiration servounit is described in U.S. Pat. No. 3,741,208. U.S. Pat. No. 5,383,449 provides for control of oxygen concentration in a breathable gas by calculation of the mole ratios and pressure in the containment vessel, and by sequentially injecting oxygen and another gas to desired pressure values. These so-called batch mixing ventilators represent one system for patient ventilation.

While such systems are very useful in hospitals and other health care facilities, smaller and more confined devices not requiring connection to pressurized air are often more appropriate for home care. Piston and bellows types of ventilators allow delivery of a predetermined volume of breathing gas at a desired pressure responsive to the initiation of inspiratory efforts by a patient. Piston based ventilators can typically be made to be more compact than bellows based ventilators, but piston ventilators typically blend pressurized air and oxygen in a high pressure blender. The resultant mixture is then drawn by a piston through a valve that reduces the pressure of the mixture. Such systems typically do not permit the use of room air and pressurized oxygen, and can result in some risk of overpressurization in the event of failure of a high pressure gas delivery valve controlling introduction of one of the breathing gas components into the high pressure blender.

Another system for blending oxygen in a ventilator is shown in International Publication No. WO 96/24402 published Aug. 15, 1996. This system is designed for mixing gases at approximately ambient atmospheric pressure, such as oxygen and air. The mixing apparatus includes a piston disposed within a pump chamber. A flow limiting inlet controls introduction of oxygen for mixing with air, and the pressure of the oxygen is limited to an acceptable maximum pressure whereby even if the oxygen valve fails, the breathing gas will not be provided at an excessive pressure. A demand valve is alternately provided for reducing the pressure of the oxygen supplied before mixing, and a pressure sensor is also provided downstream of the demand valve for detecting failure of the demand valve to shut off the supply of the oxygen to prevent overpressurization.

It would be desirable, however, to provide a piston ventilator where oxygen can be blended with gas or air where the piston causes air to be provided to the patient in a cycle which more closely approximates the patient's inhalation and expiration profile. A disadvantage of using a constant rate of piston movement within the cylinder to produce ventilation flow is that the flow is affected by changes in gas density and altitude, and thus requires the use of barometric pressure monitoring and input to control the piston movement rate. In turn, it would be desirable to monitor the flow of the gas breathed by the patient and provide oxygen blending based on the flow and feedback controls based on: the flow and the volume of gas in the piston cylinder to permit use of less expensive valve controls. It is also desirable to provide oxygen blending in such a piston system where oxygen enrichment can be provided for air remaining in the ventilator system downstream from the piston system after exhalation by the patient.

SUMMARY OF THE INVENTION

These and other objects are largely met by the oxygen blending system of the present invention. That is to say, the oxygen blending system hereof uses a piston ventilator which is sufficiently compact for home use, controls the operation of the piston to provide oxygen blending in a non-constant flow rate of breathing gas to the patient, and provides enriched oxygen to the patient side of the ventilator circuit, i.e. downstream from the piston, during piston retraction to optimize the oxygen content of all of the air inhaled by the user.

The piston ventilator of the present invention broadly includes an oxygen blending module, a primary piston-driven pressurization assembly for providing positive pressure flow of breathable gas to the patient, a secondary make-up gas module, a controller, an exhalation control system, and a patient circuit for delivering air to the patient for inhalation and exhausting exhaled air. The oxygen blending module includes a connection to a source of pressurized oxygen, a first control valve which regulates the flow of oxygen to the piston, and a flow sensor for monitoring the flow of oxygen to the piston. In addition, the oxygen blending module includes a second control valve for regulating the amount of oxygen delivered to the patient circuit to enrich the gas remaining in the patient circuit during the retraction stroke of the piston. The valves are current sensitive orifice valves responsive to signals from the controller, which preferably includes a microprocessor. The flow sensor is operatively connected to the controller to provide signals corresponding to the flow of oxygen to the primary piston-driven pressurization system.

The primary piston-driven pressurization system receives oxygen from the oxygen blending module and air or another breathable gas and is operated by a motor, gear drive and cam arm to provide a flow of blended gas therefrom. That is to say, the primary system receives a low volumetric flow of blended gas at the beginning of its retracting intake stroke building to a maximum volumetric flow of blended gas during the intermediate portion of its retracting stroke and then reducing to a low volumetric flow of air at the end of its retracting stroke before beginning the protracting stroke. When relatively large volumes of breathable gas are delivered during protraction of the piston within the cylinder, the primary system delivers a low volumetric flow at the beginning of protraction building to a maximum volumetric flow of blended gas during the intermediate portion of its protracting stroke and then reducing to a low volumetric flow of gas at the end of its protracting stroke. When the volume of gas to be provided to the patient circuit is relatively low, the flow will increase abruptly and then reduce to a smaller flow at the end of the protracting stroke. Alternatively, the movement of the motor and thus the piston may be controlled to expel the blended gas more constantly to provide a flow to the patient of sustained and substantially constant pressure.

Because the increase of the volume above the piston in the cylinder is non-linear but rather sinusoidal during intake and blending, the flow of the oxygen into the cylinder is similarly non-linear. The motor driving the piston preferably provides a virtually continuously updated signal to the controller corresponding to the position of the piston, which permits the microprocessor to calculate by integration the volume of gas in the cylinder during the retraction stroke and similarly the volume of added oxygen which should have passed by the flow sensor and should be present in the cylinder. By continuously updating the comparison between the calculated amount of oxygen in the cylinder with the actual amount of oxygen delivered to the cylinder during the retraction stroke, the controller can substantially continuously signal the first control valve to open or close to provide the desired amount of oxygen enrichment to the cylinder. Preferably, the motor is a motor capable of bi-directional movement so that an adjustable end-of-travel sensor can be provided to initialize the position of the motor with the controller and thereafter acts as a safety limiter, with the controller providing a signal to the motor to reverse direction between protraction and retraction and thereby accommodate users of different lung capacities.

The secondary make-up module uses a low-pressure blower to provide make-up air or other breathable gas to the system to compensate for leakage, in particular the leakage from around tracheal tubes inserted into the patient's windpipe or mouth. The controller provides a speed control signal to the blower to maintain the appropriate amount of pressure in the patient circuit based upon the amount of flow out of the patient circuit. The controller senses the amount of flow out of the patient circuit, which in turn operates an oxygen valve to maintain a satisfactory oxygen enriched gas in the patient circuit. The speed control signal, together with the amount of total oxygen specified to the controller, operates the second oxygen control valve to permit greater or smaller flows of oxygen to flow to the patient side of the ventilator and thus into the patient circuit for maintaining satisfactory oxygen enrichment in the patient circuit during retraction of the piston in the cylinder preparatory to initiation of inhalation. The primary flow sensor provides a signal corresponding to the volume of mixed gas leakage in the patient circuit ($V_T$). The volume of oxygen ($O_2$) introduced is known by introducing $O_2$ gas of known pressure upstream of a known orifice size for a specific period of time, yielding an oxygen volume ($V_{O2}$).

The concentration of oxygen in the make-up gas is then known by the equation:

$$V_T = V_{AIR} + V_{O2}$$

$$O_2\% = 79(V_{O2} - V_T) + 21$$

where $V_T$ is obtained by a measurement by the primary flow sensor and $V_{O2}$ is known by how long the primary oxygen control valve is open, the orifice size, and the upstream pressure.

The exhalation control system is positioned on the patient side of the ventilator for connection to the patient circuit which is connected to the ventilator and includes a flow sensor for monitoring the flow of breathable gas to the patient, pressure sensors for detecting the pressure in the patient circuit during inhalation and exhalation, and a positive end expiratory pressure control valve. The patient circuit is attached to the ventilator for connection to the exhalation control system and includes and a pneumatically controlled exhalation valve. The positive end expiratory pressure (PEEP) control valve regulates the amount of gas delivered to a diaphragm, preferably an inflatable balloon diaphragm, in the exhalation valve by selectively venting gas from the diaphragm in the exhalation control system prior to delivery to the patient circuit. By such venting, a pneumatic signal is provided through a signal conduit as the pressure on the diaphragm increases relative to the pressure in the patient circuit and the resistance of the exhalation valve to the flow of gases from the patient circuit increases. Excess gas from the diaphragm is exhausted through the PEEP control valve to the atmosphere. An increase in the pressure on the diaphragm thereby increases the amount of PEEP, that is, the pressure remaining in the patient's airway after exhalation, which in turn resists collapse of the patient's lungs and enhances the rapidity with which the patient may begin effective inhalation of the next breath.

As a result, the movement of the piston directly corresponds to the inhalation and exhalation of the patient pneumatically connected to the ventilator, with the desired amount of oxygen enrichment provided to aid the patient's respiration. The enrichment is provided notwithstanding characteristics of the intake flow of breathable gas into the piston and cylinder assembly whether it be linear or sinusoidal because the amount of oxygen added to the cylinder is constantly monitored and controlled in a closed loop system. Furthermore, the make-up air or other gas provided to the patient is oxygen enriched, and provided in connection with a positive end expiratory pressure control to enhance the rapidity with which the next breath may be inhaled. These and other advantages will be readily apparent to those skilled in the art with reference to the drawings and description set forth below.

BRIEF DESCRIPTION OF THE DRAWINGS

FIG. 2 is a block diagram of various components of the controller shown in FIG. 1 in operative relationship to controlled components of the ventilator system; and FIG. 3 is a block diagram of other components of the controller shown in FIG. 1 in operative relationship to controlled components of the exhalation control system.

DESCRIPTION OF THE PREFERRED EMBODIMENT

Figure 1:
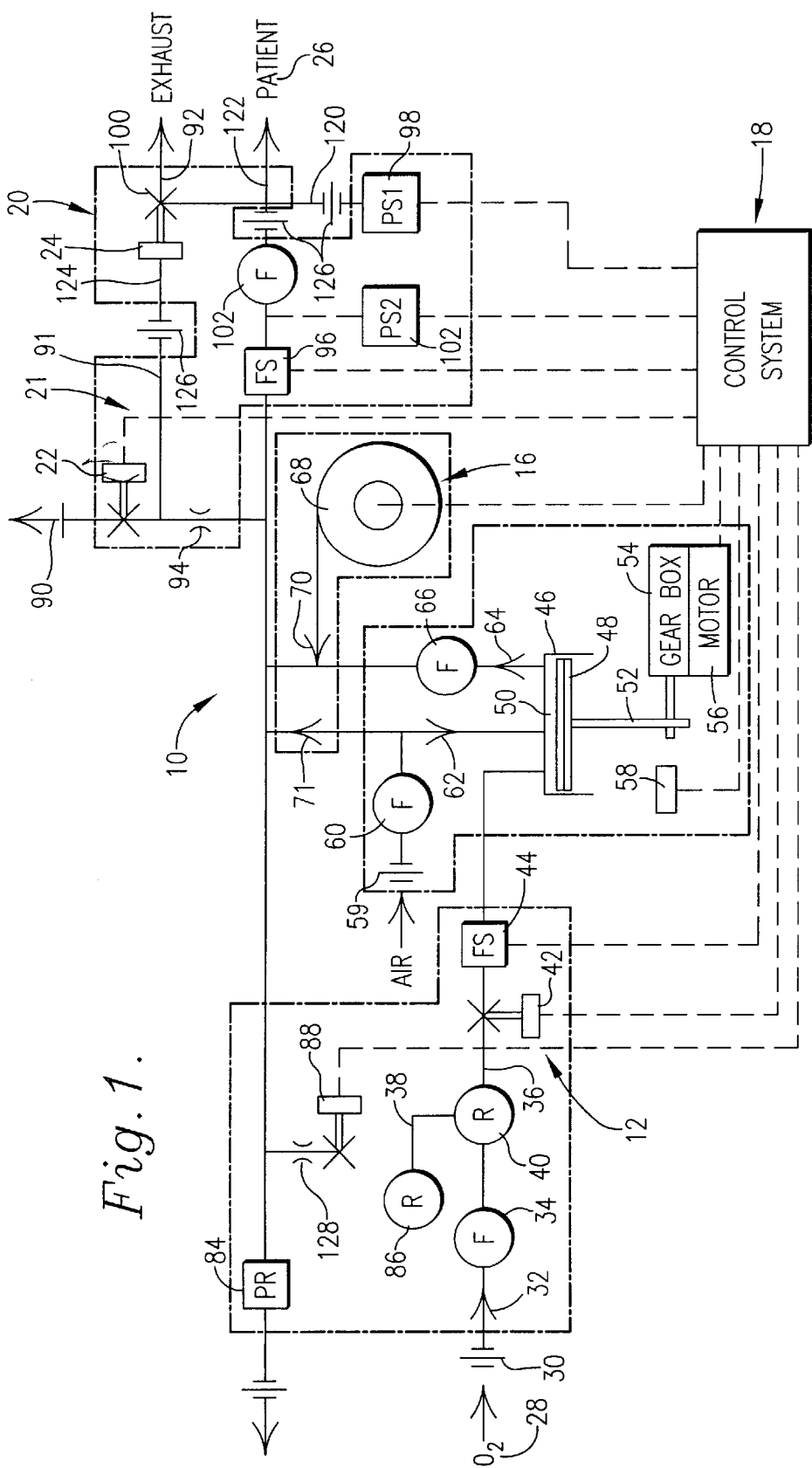
FIG. 1 is a schematic diagram of a ventilator system including an oxygen blending module, with pneumatic connections shown in solid lines and electric connections shown in dashed lines.

Referring now to the drawing, a ventilator system 10 particularly useful for assisting respiration in medical patients is shown schematically in FIG. 1 and broadly includes an oxygen blending module 12, a primary piston-driven pressurization system 14, a secondary make-up gas module 16, a controller 18, a patient circuit 20 and an exhalation control system 21 having a positive end expiratory pressure (PEEP) control valve 22. The patient circuit is detachably mounted to the exhalation control system 10 and thus is located outside an enclosure and in immediate proximity to the patient 26. The patient circuit 20 includes an exhalation control valve 24. The ventilator system 10 is particularly useful in delivering air with enhanced oxygen content in a patient-assist mode to a medical patient 26 with incomplete respiratory capabilities, but it may be appreciated that the ventilator system 10 may employ other breathable gases, for instance helium or nitrogen which may be blended with oxygen, as circumstances dictate.

The oxygen blending module 12 is connected to a source of pressurized oxygen 28 such as bottled oxygen or a connection to a central oxygen source by an oxygen fitting 30. The oxygen received from the source 28 passes through a check valve 32 and a filter 34, e.g. 40 micron mesh filter, and is divided into first and second paths 36 and 38. The first path 36 leads to the primary pressurization system 14, while the second path 38 leads to the exhalation control system 21.

The oxygen provided by the first path 36 passes from a pressure regulator 40 for providing the supplied oxygen at a substantially constant desired pressure, and then to primary oxygen control valve 42. Preferably, the regulator 40 limits pressure of the oxygen downstream from the regulator to 55 psi to maximize output, although lower settings are permissible. Advantageously, the primary oxygen control valve station 42, illustrated schematically in FIG. 1 as a single valve, is provided as two parallel current-controlled voltage sensitive orifice (VSO) valves. Current rather than voltage is used to control the VSO valves because it is less subject to variations due to temperature. The primary oxygen control valve station 42 is electrically coupled to controller 18 for receiving control signals and transmitting valve position information. A gas flow sensor 44 is provided downstream from valve 42 to monitor the flow of oxygen therepast. The gas flow sensor 44 is preferably provided as a low flow gas sensor in parallel with a flow inducing restrictor to provide a larger full scale flow capacity than the low flow gas sensor alone. The gas flow sensor 44 is electrically connected to the controller 18 for providing a signal thereto.

The primary piston-driven ventilation system 14 includes a cylinder 46 and a reciprocating piston 48 presenting a chamber 50 between the piston 48 and the cylinder 46. The piston 48 is coupled to an arm 52 which functions as a cam to move the piston 48 vertically within the cylinder 46 at the greatest rate at the middle of the stroke and at the smallest rate at the beginning and end of the stroke. The speed of the piston 48 during retraction is thus sinusoidal corresponding to the cosine of the angle between the arm and the horizontal as illustrated in FIG. 1. The arm 52 is coupled to a gear box 54 driven by a bidirectional motor 56. That is to say, the motor is capable of both clockwise and counterclockwise movement, whereby the arm 52 does fully rotate but rather reverses direction during transition between the protracting and retracting stroke and vice versa. An end of travel sensor 58 is adjustably mounted for operative engagement with the piston 48 at the bottom of the retracting stroke and electrically coupled to the controller 18 to signal the controller 18 to initialize the position of the motor 56 and thus the piston 48 at start up and as a safety device during continued operation. By initializing the position of the motor 56, the controller 18 controls the operation of the motor 56 to change its direction of rotation and thus the length of the stroke of the piston 48 within the cylinder 46 at the appropriate position based on the motor position and a preselected total volume setting provided by the operator to the controller 18. The adjustment feature permits the amount of enriched oxygenated air or other gas supplied to the patient 26 to be varied based on the patient's lung capacity. The motor 56 is preferably a brushless direct current motor which is electrically coupled to the controller 18 to provide a continuous signal corresponding to the number of revolutions and position of the motor drive and thus the arm 52. Air or other breathable gas is supplied to the primary piston-driven ventilation system 14 from the ambient air inlet 59 which passes through a filter 60, e.g. a 0.3 micron filter, and through a check valve 62. The air is mixed with the oxygen supplied from the oxygen blending module 12 in the chamber 50, and then discharged through check valve 64 before passing through another filter 66, such as a 50 by 250 mesh filter leading to the exhalation control system 21.

The secondary make-up gas module 16 primarily includes a low-pressure/low-volume blower 68 delivering air through a check valve 70 into the patient circuit 20 downstream from filter 66 and is prevented from flowing back into the chamber 50 by check valve 71. The blower 68 typically operates constantly to supply a flow of breathable gas such as air obtained from the ambient air and at higher speeds may generate as much as 20 cm $H_2O$ peak pressure to make-up air lost through leakage of up to 10 liters per minute of air in the patient circuit, e.g., around a tracheal tube or the like. The operating speed of the blower 68 is controlled by the controller 18 in response to a signal corresponding to the pressure in the exhalation control system 21 provided to the controller as sensed by a pressure sensor 98. The blower 68 thus not only compensates for leaks in the system but also maintains PEEP levels and provides a flow, when a patient initiates a breath, for which to trigger a breath.

The controller 18 includes a microprocessor 72 which is programmed with operating instructions. As shown in FIG. 2, the controller 18 also includes a flow sensor signal conditioner 74 which receives input from the flow sensor 44, with the signal being delivered to the microprocessor 72 via an analog to digital converter 76. Similarly, the microprocessor 72 provides a signal to a blender valve drive 78 which provides sufficient current to operate the VSO valves of the primary oxygen control valve station 42 through a digital to analog converter 80. Also as shown in FIG. 2, the microprocessor 72 receives a signal from a motor position monitor 82 operatively connected to motor 56 which in turn senses the number of revolutions and position of the motor 56 and thus the arm 52 and piston 48 and in turn signals the motor 56 to protract or retract the piston 48. As shown in FIG. 3, the controller 18 includes other components to perform functions relating to sensing the PEEP and operating the PEEP valve 22 in response thereto. The controller also includes a pressure sensor signal conditioner 112 which receives input from the first pressure sensor 98, with the signal being delivered to the microprocessor 72 via an analog to digital converter 114. Similarly, the microprocessor 72 provides a signal to a PEEP valve controller 116 mounted on PEEP valve 22 through a digital to analog converter 118. The PEEP valve 22 is then in turn connected to the exhalation valve 24 by a signal conduit 91 as shown in FIG. 1 to provide resistance based on PEEP by providing a pneumatic signal and thereby controls the PEEP at the end of the exhalation of the patient's breath.

The exhalation control system 21 receives blended air from filter 66 and make up air from blower 68 through check valve 70. Excess pressure may be relieved by actuating manual pressure relief valve 84. The second path 38 is provided as a conduit which advantageously may be connected to regulator 40 to obtain oxygen at 55 psi instead of directly from the supply 28 which is typically at 80 psi. The routing of the second path 38 from regulator 40 permits the use of a pressure regulator 86 which steps down the pressure from 55 psi to about 15 psi. Oxygen is provided through second path 38 through pressure regulator 86 and then to make-up oxygen control valve 88 for delivery through a flow restrictor 128 to the exhalation control system 21 for delivery to the patient circuit 20. Make-up oxygen control valve 88 may be a circuit-controlled voltage sensitive orifice valve or alternatively a digital valve which is electrically connected to controller 18 as is blower 68. The amount the make-up oxygen control valve 88 is permitted to open to admit oxygen from second path 38 is determined by the volume of air flowing across the primary flow sensor, and thus proportional to the flow of air or other breathable gas delivered by the blower 68 as controlled by the controller 18 based on the desired total amount of oxygen to be delivered to the patient. It is intended that the pressure of the oxygen supplied through regulator 86 will exceed the pressure generated by the blower 68 to ensure that the gas delivered to the patient circuit 20 will be suitably oxygen enriched.

The exhalation control system 21 includes the PEEP control valve 22, signal conduit 91, a flow restrictor 94, a flow sensor 96, a first pressure sensor 98, a second pressure sensor 102, and a filter 104. The PEEP control valve 22 serves to vent excess air to the atmosphere through vent 90 to regulate the pressure on the diaphragm side of the exhalation control valve 24, which in turn regulates the pressure in the patient circuit 20 to the PEEP setting entered by the operator. The PEEP valve 22 is electrically coupled to the controller 18 to regulate the amount of air permitted to be vented through vent 90. When the PEEP valve is at full bypass or open, an inflatable diaphragm in the exhalation control valve 24 of the patient circuit will be fully deflated giving nearly a 0 cm H$_2$O PEEP. When the PEEP valve 22 is fully closed, the exhalation valve 24 is closed to prevent gas from passing through the exhalation valve 24 to exhaust 92 and thus gas cannot escape during inhalation. Under these conditions, pressure in the patient circuit 20 and the exhalation control system 21 can be arbitrarily large depending on the amount of gas contained in the available volume until pressure relief valve 84 is activated. Similarly, the PEEP control valve 22 is pneumatically coupled to exhalation control valve 24 to decrease the pressure in the patient circuit 20 when the PEEP pressure rises above the predetermined valve. On the other hand, when the PEEP pressure falls below the predetermined value, the controller 18 signals the blower 68 to increase its speed and thereby increase the pressure in the patient circuit. As a safety measure the PEEP valve 22 is normally open to deflate the inflatable diaphragm and allow the patient to breathe in the event of a failure. The PEEP control valve 22 is pneumatically connected to the exhalation control valve 24 by a signal conduit 91. The PEEP control valve 22 is pneumatically connected to the exhalation control valve 24 and includes a body defining therein a enclosure and the inflatable diaphragm is located within the enclosure which regulates the restriction through which the patient 26 must exhale air delivered to exhaust 92 to the atmosphere. One exhaust valve 24 which has been found to be acceptable for use is commercially available as Part No. 6350 which is a component of either patient circuit Model No. 6462 or 6461 available from Nellcor Puritan Bennett of Pleasonton, Calif.

Oxygen enriched air is delivered to PEEP valve 22 through a flow restrictor 94, with the main flow of air delivered by the primary piston-driven ventilation system through a flow sensor 96 which monitors the delivery of air to the patient. The size of the opening of the PEEP valve 22 and the pressure in the patient circuit 20 as determined by first pressure sensor 98 determine the rate of flow of gases out of the PEEP valve 22. Because the PEEP valve 22 and the restrictor 94 are in series, the flow of gas out of the PEEP valve 22 is also the flow through the restrictor 94, as well as any minimal amount of gas flowing to or from the diaphragm through the signal conduit. The rate of flow of the gases through the restrictor 94 induces a pressure drop across the length of the restrictor 94. This causes pressure on the backside or signal conduit side of the diaphragm to be less than the pressure at the patient side (i.e the front side) of the diaphragm. This pressure difference reduces the resistance of the exhalation valve 24, allows gases in the patient circuit 22 escape out of the exhalation valve 24, and ultimately decreases the pressure in the patient circuit 20. By controlling the rate of flow of gases through the restrictor 94, the pressure in the patient circuit 20 and PEEP may also be controlled.

During exhalation, the piston 48 is retracted and thus air or other breathable gas is supplied to both PEEP valve 22 and exhalation control valve 24 by a combination of make-up air from blower 68 and oxygen supplied through patient circuit oxygen control valve 88, and from the exhalation of the patient:26. A first pressure sensor 98 is in immediate proximity to the patient 26 in the conduit delivering oxygen-enriched air to the patient 26, and is electrically connected to the controller 18 to signal the PEEP valve 22 how much air is to be exhausted to the atmosphere through exhaust 92, and therefore how much of the make-up air and breath exhaled by the patient is delivered to the exhalation con-trol:valve inflatable diaphragm. The first pressure sensor 98 is electrically connected to the controller 18 and thus provides the controller 18 with a signal corresponding to the pressure of the gas being provided to the patient 26 during inhalation, and PEEP at the end of exhalation. A second pressure sensor 102 is electrically connected to the controller 18 and provides a backup and validation of the first pressure sensor 98 by monitoring the pressure in the exhalation control system 21 and providing a second pressure signal to the controller.

The PEEP valve 22 is normally open and indirectly controls the resistance of the exhalation valve 24 to the flow of gas from the breathing circuit to the atmosphere. By increasing or decreasing this resistance, the exhalation valve 24 can decrease or maintain the amount of gas in the patient circuit and thereby decrease or maintain the pressure in the patient circuit 20. The PEEP valve 22 regulates the pressure applied to the exhalation valve 24 by controlling the amount of air delivered from the patient circuit 20 to the exhaust 92. The more gas delivered by the PEEP valve 22 to the vent 90, the lower the pressure on the diaphragm on the exhalation valve 24 that covers the exhalation opening 100 of the exhalation control valve 24. The greater the restriction in the PEEP valve 22, and thus the less gas delivered to the vent 90, the greater the pressure on the diaphragm of the exhalation control valve 24 and thus the greater the expansion of the diaphragm within the enclosure thereby reducing the size of the restriction to increase the resistance provided during exhalation by the patient 26. The amount of resistance to exhalation is proportional to the pressure of the gas supplied to the diaphragm and thus proportional to the amount the PEEP valve 22 is open. The signal supplied to open or close the PEEP valve 22 by the controller 18 is determined by the first pressure sensor 98.

The primary flow sensor 96 provides a signal corresponding to the volume ($V_T$) of mixed gas leak in the patient circuit. The volume of oxygen introduced is known by introducing $O_2$ gas at a known pressure upstream of a known orifice size for a specific period of time. Alternatively, a voltage sensitive orifice (VSO) valve may be used in place of the fixed orifice and a digital valve. The oxygen concentration of the make-up gas is then known via the equation:

$$V_T = V_{AIR} + V_{O2};$$

and $$O_2\% = 79(V_{O2}V_T) + 21$$

The controller 18 in turn sends operating signals to blower 68 and patient circuit control valve 88. A filter 104, such as a 40 mesh filter, provides final filtration of the air with enriched oxygen prior to delivery to the patient.

The patient circuit 20 is connected to the exhalation control system 21 by flexible conduits 120, 122 and 124 which lead to hose connectors 126 which are respectively operatively connected to the first pressure sensor 98, the filter 104 delivering breathable gas to be inhaled by the patient, and the signal conduit 91 leading to PEEP valve 22.

In use, the ventilator system 10 hereof provides respiratory assistance to patient 26 so that the respiration rate of patent 26 directly corresponds to the rate of reciprocation of the piston 48 within the chamber 50. Thus, with each protracting movement of the piston 48 within the cylinder 46, patient inhales, and with each retracting stroke of the piston 48 within the cylinder 46, the patient exhales. Prior to operation of the ventilator system, the operator selects and sets the controller 18 at a desired level of oxygen enrichment, for example within a range of 21% to 100% total oxygen received by the patient and additionally selects a target pressure level for PEEP within a typical range of 0 cm $H_2O$ providing no resistance in the exhalation valve during the exhale segment of the patient's breath to 20 cm $H_2O$ providing full resistance in the exhalation valve 24.

During each retracting stroke of the piston 48, the motor position monitor 82 signals the position of the piston 48 within the cylinder 46 and permits the controller 18 to calculate the volume of the chamber 50. For any desired amount of oxygen enrichment, this produced a corresponding calculation of the amount of added oxygen which should be present in the chamber. The calculation of volume and thus the amount of added oxygen present in the chamber 50 is continuously updated during the retracting stroke of the piston 48. Because the speed of retraction of the piston 48 is not linear but rather sinusoidal, the volume in the chamber 50 changes sinusoidally.

Flow sensor 44 thus determines the flow rate of oxygen delivered to chamber 50 on a continuous basis. Its signal is received by the controller 18 and the flow rates are integrated to yield the amount of oxygen actually delivered to the chamber 50. If the controller 18 determines that the accumulated oxygen delivered to the chamber is insufficient, it signals the primary oxygen control valve station 42 to open and permit additional oxygen to flow past flow sensor 44. If this produces oxygen in the chamber 50 in excess of the target amount prior to the end of the retracting stroke as determined by the integrated value, calculated by the controller from the flow rates determined by flow sensor 44, the controller signals the primary oxygen control valve station 42 to close and thereby reduce the flow of oxygen past flow sensor 44 and delivered to chamber 50

During the retraction stroke of the piston 48, the patient exhales. Exhalation by the patient is primarily delivered through exhalation control valve 24 to exhaust 92. The inflation of the diaphragm within the exhalation control valve 24 causes the flow of exhaled air through the exhalation opening 100 to be restricted, and the patient must exert some effort to overcome the restriction depending on the pressure of the gas supplied to the inflatable diaphragm. The amount of the restriction may be controlled by the signal supplied by the controller 18 to the PEEP valve 22 to determine the amount of air permitting to vent therefrom. Because of leakage around tracheal tubes in tracheostomies or through conduit connections, the majority of the air supplied to the exhalation control valve 24 is delivered by blower 68. Because a portion of the air remaining in the inhalation control system 21 will be inhaled when the piston 48 protracts, it is desirable to ensure that the air inhaled by the patient 26 is properly oxygenated. To that end, supplemental oxygen is delivered to the patient circuit 20 through make-up oxygen control valve 88 and its opening and closing as well as the speed of and thus the flow of gas delivered by the blower are determined by the controller 18 based on the signal provided by the first pressure sensor 98. If a PEEP setting of zero is provided to the controller 18, the blower 68 will shut off and the make-up oxygen control valve 88 will be closed. In the event of a leak (up to 10 liters per minute) and in the presence of PEEP (up to 20 cm $H_2O$), the blower 68 is energized by the control logic to provide the make-up air to fulfill the requirements of the leak. While doing this, PEEP pressure is maintained. The air provided by the blower 68 is non-$O_2$ enriched air. If $O_2$ levels are being maintained, supplemental oxygen is provided through the second path 38 as referenced above.

Once the piston 48 reaches the end of its retracting stroke as sensed by the motor position monitor and determined by the controller 18 based on motor position and speed and the preset overall volume desired for delivery to the patient 26, the controller 18 signals the motor 56 to reverse its direction and begin protraction of the piston 48 within the cylinder 46. As the piston protracts, oxygen-enriched air is expelled from the chamber 50 through the check valve 64 for delivery to the patient circuit 20 and ultimately inhalation by patient 26 after passage through filter 104. Thus, protraction of the piston 48 corresponds to inhalation 26 by the patient due to the delivery of pressurized air to inflate the patient's lungs.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby states their intent to rely on the Doctrine of Equivalents to determine and assess the reasonably fair scope of their invention as pertains to any apparatus not materially departing from but outside the literal scope of the invention as set out in the following claims.

What is claimed is:

1. A patient ventilator comprising:
   a piston and cylinder assembly including a cylinder and a piston reciprocally received in said cylinder for movement along a retracting gas intake stroke and a protracting gas expelling stroke to define a variable volume chamber therebetween;
   a patient circuit for delivering breathable gas from said piston and cylinder assembly to a patient during patient inhalation;

a controller connected to said piston and cylinder assembly for receiving input corresponding to the position of the piston within the cylinder during the intake stroke; and an oxygen blending module fluidically connected to said chamber of said piston and cylinder assembly for controlling delivery of oxygen from an oxygen source to the piston and cylinder assembly for blending with the breathable gas in the chamber, said oxygen blending module including a first oxygen control valve operatively connected to said controller and a flow sensor for providing a signal to said controller representative of an amount of oxygen delivered from the first oxygen control valve, wherein said controller calculates a target amount of oxygen in said piston and cylinder assembly based on the position of the piston during the intake stroke, calculates a difference between said target amount and a calculated actual amount of oxygen delivered past said flow sensor based on the signal provided by the flow sensor and directs a control signal for opening and closing the first oxygen control valve based on said calculated difference during said intake stroke.

2. A patient ventilator as set forth in claim 1, wherein said oxygen blending module includes a first path for delivering oxygen to said first oxygen control valve and a second path for delivering oxygen downstream from said piston and cylinder assembly to said patient circuit.

3. A patient ventilator as set forth in claim 2, wherein said second path includes a second oxygen control valve in operative communication with said controller for controlling the amount of oxygen delivered from said second path to said patient circuit.

4. A patient ventilator as set forth in claim 3, including a secondary source of pressurized breathable gas in communication with said patient circuit.

5. A patient ventilator as set forth in claim 4, wherein said secondary source includes a blower for providing a constant flow of gas in addition to said oxygen received from said second path.

6. A patient ventilator as set forth in claim 5, wherein said second oxygen control valve is operatively connected to said controller to open and close in response to a signal received from said controller.

7. A patient ventilator as set forth in claim 6, wherein said blower is operatively connected to said controller whereby the flow of gas supplied by said blower to said patient circuit is controlled by said controller.

8. A patient ventilator as set forth in claim 7, including a primary pressure sensor for providing a signal to said controller indicative of leakage of gas from said patient circuit, and wherein said blower is operatively controlled by said controller in response to said leakage signal.

9. A patient ventilator as set forth in claim 1, said patient circuit including an exhalation valve including a shiftable element responsive to a pneumatic signal for shifting between an open position, a closed position and a plurality of intermediate positions in correspondence with said pneumatic signal, said patient ventilator further including a signal conduit for delivering gas to said exhalation valve as said pneumatic signal, a vent valve coupled with said signal conduit for selectively venting gas therefrom for selectively altering said pneumatic signal and in operative communication with said controller, a pressure sensor connected to said controller and positioned in said patient circuit for sensing the pressure therein as the PEEP pressure and producing a PEEP pressure signal representative thereto, and means positioned upstream of said vent valve for creating a pressure differential between the gas pressure in said signal conduit and the gas pressure at the pressure sensor, said controller operating said vent valve based on a comparison between the PEEP pressure signal and a preselected target PEEP pressure.

10. A method of blending oxygen with breathable gas in a piston ventilator comprising the steps of:

providing a pressurized source of oxygen and a piston ventilator, said ventilator including a piston and cylinder assembly having a reciprocating piston shiftable within a cylinder during a retracting gas intake stroke and a protracting gas expelling stroke to define therebetween a variable volume chamber, a first path for fluidically connecting said oxygen source to said piston and cylinder assembly to deliver oxygen to said chamber, said first path including a flow sensor and a first oxygen control valve, a patient circuit located fluidically downstream from said piston and cylinder assembly for delivering breathable gas to a patient, and a controller connected to said piston and cylinder assembly, said flow sensor and said first control valve;

retracting said piston within said cylinder to intake breathable gas into said chamber;

monitoring the position of said piston within said cylinder during retraction;

delivering a signal to said controller from said piston and cylinder assembly representative of said position of the piston;

delivering oxygen from said source through said first path to said chamber of said piston ventilator during retraction of said piston;

monitoring a flow of oxygen past said flow sensors along said first path;

delivering a signal to said controller from said flow sensor representative of an amount of oxygen flowing past the flow sensor;

calculating in said controller the amount of oxygen delivered to said chamber of said piston and cylinder assembly from said first path during retraction of the piston based on said signal from said flow sensor;

comparing said calculated amount of delivered oxygen to a preselected value corresponding to a target amount of oxygen desired to be delivered to said piston and cylinder assembly based on the piston position signal and calculating a difference between the calculated amount and the preselected value;

generating a control signal in said controller corresponding to said calculated difference and delivering said control signal to said oxygen control valve; and adjusting the flow of oxygen to be delivered to said chamber through said oxygen control valve responsive to said control signal.

11. A method of blending oxygen with breathable gas in a piston ventilator as set forth in claim 10, including providing a secondary source of breathable gas to said patient circuit.

12. A method of blending oxygen with breathable gas in a piston ventilator as set forth in claim 11, wherein the ventilator includes a second path fluidically connected to said oxygen source and to said patient circuit for delivering oxygen to said patient circuit, said second path including a second oxygen control valve, and including the step of providing supplemental oxygen to said patient circuit through said second path during retraction of said piston.

* * * * *